United States Patent [19]
Wheeler

[11] Patent Number: 5,993,748
[45] Date of Patent: Nov. 30, 1999

[54] HOT GAS EXTRACTION DEVICE FOR VOLATIZING AT LEAST ONE SUBSTITUENT OF A MATERIAL

[76] Inventor: David L. Wheeler, Box AK, Elephant Butte, N.Mex. 87935

[21] Appl. No.: 09/070,134

[22] Filed: Apr. 29, 1998

[51] Int. Cl.⁶ ...................................................... A61L 9/03
[52] U.S. Cl. .................. 422/125; 422/124; 422/306; 422/307; 392/390; 392/391; 131/173; D27/162
[58] Field of Search ................... 422/4, 5, 120, 422/123–125, 306, 307; 392/386, 390, 391, 393, 394; 131/173; D27/162

[56] References Cited

U.S. PATENT DOCUMENTS

| | | | |
|---|---|---|---|
| 931,029 | 8/1909 | Blood | 422/125 |
| 1,180,241 | 4/1916 | Class | 422/125 |
| 2,047,973 | 7/1936 | Lawton et al. | 422/5 |
| 2,542,529 | 2/1951 | Hunt | 422/125 |
| 2,737,572 | 3/1956 | Ernst | 422/306 |
| 3,959,642 | 5/1976 | Turro | 422/125 |
| 4,133,318 | 1/1979 | Gross et al. | 131/173 |
| 4,219,032 | 8/1980 | Tabatznik et al. | 131/173 |
| 5,651,942 | 7/1997 | Christensen | 422/125 |

Primary Examiner—Terrence R. Till
Assistant Examiner—Fariborz Moazzam
Attorney, Agent, or Firm—Robert W. Becker & Associates

[57] ABSTRACT

An extraction device utilizing hot air or gas for volatizing at least one substituent of a material is provided. The device has a container for holding material. The device also has a cap that is provided with holes leading from the exterior thereof to a chamber in the cap. The cap is adapted to be seated on the container so that the chamber of the cap communicates with an open end and a chamber of the container. A non-flame type heating unit is disposed in the chamber of the cap for heating gas. Gas is caused to pass through the holes of the cap, into the chamber thereof, through the chamber of the container and out of a discharge opening thereof.

17 Claims, 2 Drawing Sheets

HOT GAS EXTRACTION DEVICE FOR VOLATIZING AT LEAST ONE SUBSTITUENT OF A MATERIAL

BACKGROUND OF THE INVENTION

The present invention relates to a hot gas extraction device, in other words an extraction device that utilizes hot gas, such as air, for volatizing at least one substituent of a material.

Herbs, plants and other vegetable matter contains a number of beneficial resins, oils and fragrances, which have a number of varied applications in the medical and industrial fields as well as for home use. To extract these beneficial substituents or active ingredients, primarily in the form of gas or vapor, it is known to incinerate the material. Unfortunately, since various substituents of a material vaporize at different temperatures, incineration is an unsatisfactory procedure. In addition, where the vapors are to be inhaled or are to be used for aroma therapy, incineration produces not only undesirable by-products, but also carcinogens.

It is therefore an object of the present invention to provide an effective and economical extraction device for volatizing at least one substituent of a material, with such device overcoming the draw backs of the heretofore known devices.

BRIEF DESCRIPTION OF THE DRAWINGS

This object, and other objects and advantages of the present invention, will appear more clearly from the following specification in conjunction with the accompanying schematic drawings, in which.

SUMMARY OF THE INVENTION

Figure 1:
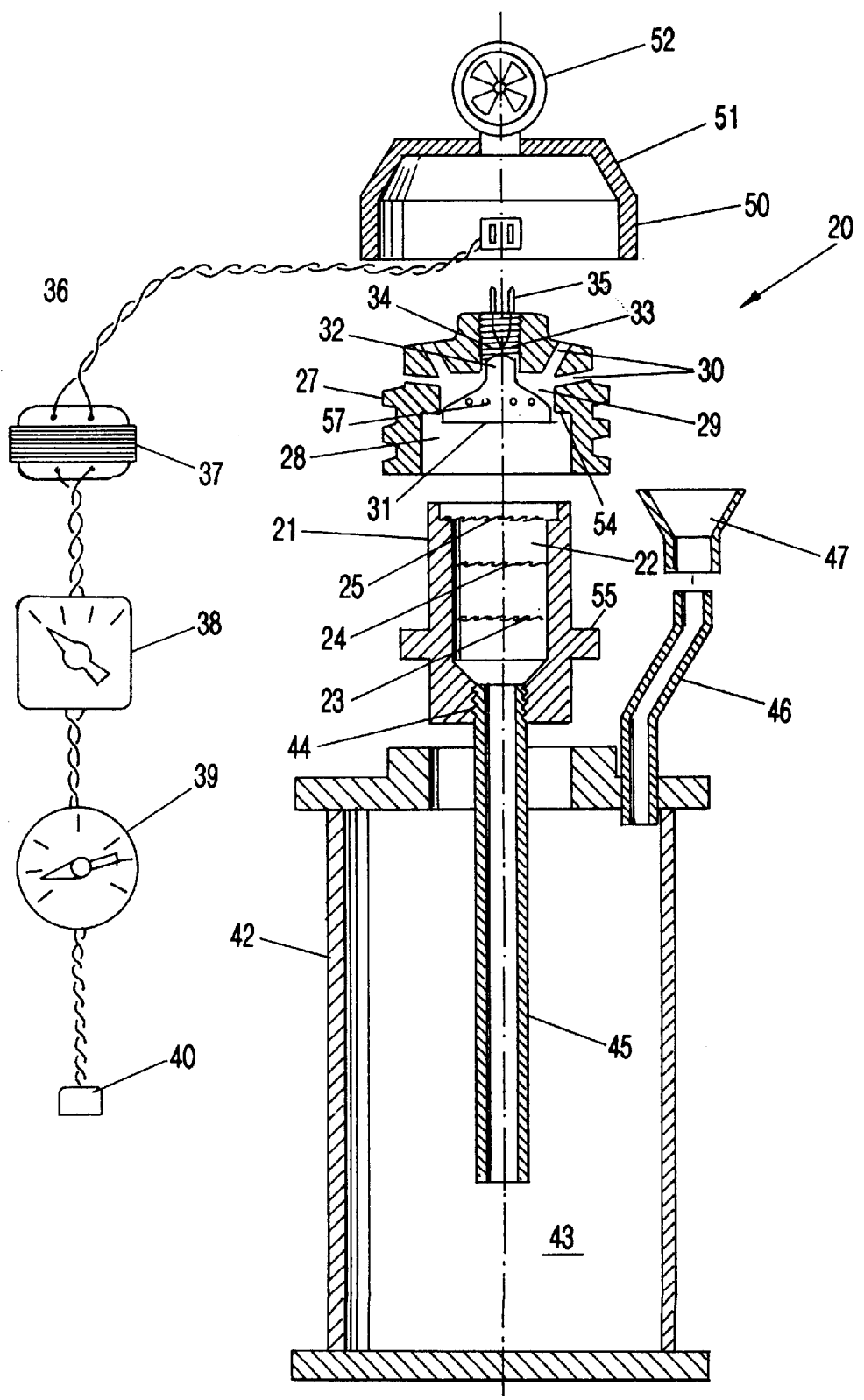
FIG. 1 illustrates one exemplary embodiment of an inventive extraction device that heats up air or other gas to then effect volatization.

The inventive hot gas extraction device comprises: a container designed for holding material and having a first chamber that communicates with an open end of the container; a cap having holes leading from the exterior thereof to a second chamber that is provided within the cap, with the cap being adapted to be seated on the container such that the second chamber of the cap communicates with the open end, and hence the first chamber, of the container; a non-flame type heating means disposed in the second chamber of the cap for heating gas; and means to cause gas to pass through the holes of the cap, into the second chamber thereof, through the first chamber of the container, and out of a discharge open thereof.

By controlling the temperature to which the air or gas that is drawn through the inventive extraction device is heated, those substituents that are desired to be extracted from the material contained in the device can be volatized. Thus, especially for medical purposes and aroma therapy, one substituent at a time can be volatized. The Inventive extraction device thus also allows separation of the various chemical substituents of a material; this is particularly useful for industrial applications. In contrast to the incineration of material, undesirable substituents can be left behind. Above all, the production of carcinogens is avoided.

Further specific features of the present invention will be described in detail subsequently.

DESCRIPTION OF PREFERRED EMBODIMENTS

While the various features of this invention are hereinafter illustrated and described as providing a hot air or gas extraction device to be used as an inhalant delivery system, it is to be understood that the various features of this invention can be utilized singly or in various combinations thereof to provide a hot air extraction device for other systems, including industrial and domestic applications, for various extractions, aroma therapy, fragrance dispersion, etc.

Therefore, this invention is not to be limited to only the embodiments illustrated in the drawings, because the drawings are merely utilized to illustrate one of the wide variety of uses of this invention.

Referring now to the drawings in detail, FIG. 1 illustrates one exemplary embodiment of the hot gas extraction device of this invention, which is generally indicated by the reference numeral 20. The inventive device includes a bowl or container portion 21 that is provided with a chamber 22 for holding material which is to have at least one of its substituents extracted, for example by having such substituent or substituents volatized with the air or gas that is heated by the device 20. In order to retain the material in the chamber 22, screens or filters 23, 24 are provided, such as stainless steel screens or screens made of polymeric material. At least one of these screens 23, 24, and preferably both of them, are removable for loading and cleaning purposes. A further screen or filter 25 can be disposed near the top of the container 21. Such screens also serve to modulate or regulate the temperature of the hot air flowing therethrough by absorbing and exchanging heat therefrom. In the illustrated embodiment, the container 21 has a tapered configuration near its bottom end, the purpose of which will be described in detail subsequently.

A cap 27 is provided that is to be placed over or otherwise connected to the container 21. The cap 27 has a chamber 28 that communicates with the chamber 22 of the container 21 when the cap 27 is placed upon the open end of the container 21. The upper end of the cap 27, in other words that end that is remote (opposite) from the container 21, is provided with a recessed portion 29 of the chamber 28; in other words, the recessed portion 29 has a smaller diameter than does the remainder of the chamber 28. Holes or bores 30 are provided in the cap 27 and lead from the exterior of the cap to the recessed chamber portion 29 to allow air from the outside, or gas from a suitable container, to be drawn or forced into the recessed chamber portion 29 for a purpose to be described in detail subsequently. A heating element 31, and in particular an electric, non-flame type heating means, is disposed in the recessed chamber portion 29. This heating element is connected to the cap 27, for example by being screwed thereto, whereby the portion 32 of the heating element 31 that is remote from the chamber 28 is provided with external threads that cooperate with internal threads provided in the bore 33 in the upper part of the cap 27. Electrical connection means 34 that lead to the heating element 31 are also provided. Further electrical connection means 35 are provided on the cap 27. Such further electrical connection means 35 can be in the form of a plug that can be connected to a power source, or can be an electrical wire that leads directly from the electrical connection means 34 to a power source. In the illustrated embodiment, it is contemplated that a wire 36 will lead to a transformer 37, for example a 12 volt transformer. The transformer 37 can be connected to a rheostat 38, for example a 4-position rheostat, for controlling the power to the hot air extraction device 20 to thereby control the temperature of the heating element 31 to thereby regulate which substituents of the material contained in the chamber 22 will be volatized. To prevent overheating, a timer switch 39 can also be provided, for example a 60 second timer switch. An electrical wire or lead 40 can then lead to a power source, such as a wall plug. It should be noted that in place of the 12 volt transformer 37, a battery pack or any 12 volt supply could also be provided, and could even be connected directly to the hot air extraction device 20.

The container 21 can be placed on the barrel or tank 42, thus allowing the interior 43 of the barrel 42 to communicate with the exit or discharge opening 44 of the container 21 to allow communication between the chamber 22 of the container 21 and the interior 43 of the barrel 42. A hollow stem tube 45 can be connected to the bottom of the container 21, for example by being threaded to the discharge opening 44 thereof. The use of the stem tube 45 is particularly expedient if the barrel 42 is to be provided with water or other liquid for cooling and/or filtering the vapor that is discharged from the container 21, which then bubbles through the water or other liquid. A separate filter could also be provided in the barrel 42, or even in the stem tube 45. For cooling purposes, iced water could be provided or other cooling means could be provided in or around the barrel. A discharge tube 46 provides communication from the interior 43 of the barrel 42 to the outside air. If the hot air extraction device 20 is to be used as an inhalant delivery system, a person using the device could draw in or inhale vapors, which have preferably been cooled in the barrel 42, directly from the discharge tube 46 and/or through a flexible, replaceable tube leading from the discharge tube 46. On the other hand, if the hot air extraction device 20 is to be used for aroma therapy or fragrance dispersion, a trumpet 47 can be placed upon the free end of the discharge tube 46 in order to disperse the vapors into the ambient air.

Where the vapors produced in the hot air extraction device 20 are to be conveyed into a room or to a further location, mechanical means to aid in either drawing the air and vapors through the device or for pushing the air and vapors through the device can be provided. For example, a non-illustrated device for pulling the air and vapors through the hot air extraction device 20 could be provided on the discharge tube 46. Alternatively, a forced air attachment 50 could be disposed over the cap 27. This forced air attachment 50 comprises a cover portion 51 as well as a fan 52 that is disposed on or in the cover portion 51. Such a fan could be a rotary fan, such as a squirrel cage type fan. Electrical power can be provided to the fan 52 by appropriate electrical leads. If the forced air attachment 50 is used, appropriate socket means could be provided therein for mating with the electrical connection means 35 of the cap 27.

In the illustrated embodiment, the various components fit together via a slip fit. For example, the cap 27 is slip fit over the container 21, whereby the upper rim of the container 21 rests against the shoulders 54 formed by the reduction of the chamber 28 to the recessed chamber portion 29. Similarly, the container 21 is slip fit into the barrel 42, whereby the collar 55 of the container 21 limits the amount by which the container 21 can extend into the barrel 42. This collar 55 also serves to facilitate removal of the container 21 from the barrel 42. Similarly, the trumpet 47 is slip fit over the discharge tube 46, and the forced air attachment 50 is slip fit over the top of the cap 27, in which case the configuration of the forced air attachment 50 is such that either the holes 30 in the cap 27 are not covered by the cover portion 51 and/or the cover portion 51 is provided with appropriate holes itself so that air can be provided to the chamber portion 29 of the cap 27.

To provide a better seal between the various components of the hot air extraction device 20, seals or gaskets could be provided; for example, O rings could be provided in appropriate channels of the components. Alternatively, or in addition thereto, the various components could be bolted or screwed together.

The hot air extraction device 20 operates as follows. To begin with, the device 20 is plugged in or otherwise turned on so that the heating element 31 can obtain the appropriate temperature; this can be regulated by the rheostat 38. The heating element 31 is preferably a coil or spiral type heating element with spaces or gaps between the coils. A large surface area for heating air or other gas is thus provided, and the heating element 31 is provided with holes 57 so that air can travel through the heating element. In particular, air enters the recessed chamber portion 29 through the air inlet holes 30 of the cap 27. The air then passes through the holes 57 of the heating element 31 and is heated thereby. Due to the unique configuration of the chambers of the cap 27, the presence of the various holes, which are preferably offset relative to one another, and due to the heating of the air therein, turbulence is created within the cap 27. This turbulence causes fluidization or suspension of the material disposed in the chamber 22 of the container 21, thus providing a larger surface area. When air is caused to be drawn or otherwise pass through the hot air extraction device 20, either by a person inhaling via the discharge tube 46, or by means of the forced air attachment 50, heated air is drawn down through the container 21, and more air is drawn into the cap 27. The heated air that is drawn through the chamber 22 of the container 21 heats the material therein, and in conformity with the temperature of the air causes volatization of those substituents of the material which are intended to be extracted; burning or carbonization of the material is avoided. Air and volatized matter is then drawn or pushed through the discharge opening 44 of the container 21 and is discharged either directly through the discharge tube 46, or first enters the barrel 42, where the vapors can, if desired, be first cooled before being discharged or inhaled through the discharge tube 46. Inhaled vapors are preferably cooled to room temperature or even lower.

As discussed previously, the bottom end of the chamber 22 of the container 21 can have a tapered configuration. This has been found to assist in the discharge of vapors from the chamber 22. It also speeds up the velocity of air flow via the Venturi principle.

Although the embodiment of the inventive hot air extraction device 20 illustrated in FIG. 1 provides for a direct connection of the heating element 31 to the cap 27, it has also been found according to the teachings of this invention that other configurations are possible. For example, reference is now made to FIG. 2, wherein another exemplary embodiment of this invention is shown and is generally indicated by the reference numeral 20A, wherein parts thereof similar to the hot air extraction device 20 of FIG. 1 are indicated by like reference numerals that where appropriate are followed by the reference letter A.

Figure 2:
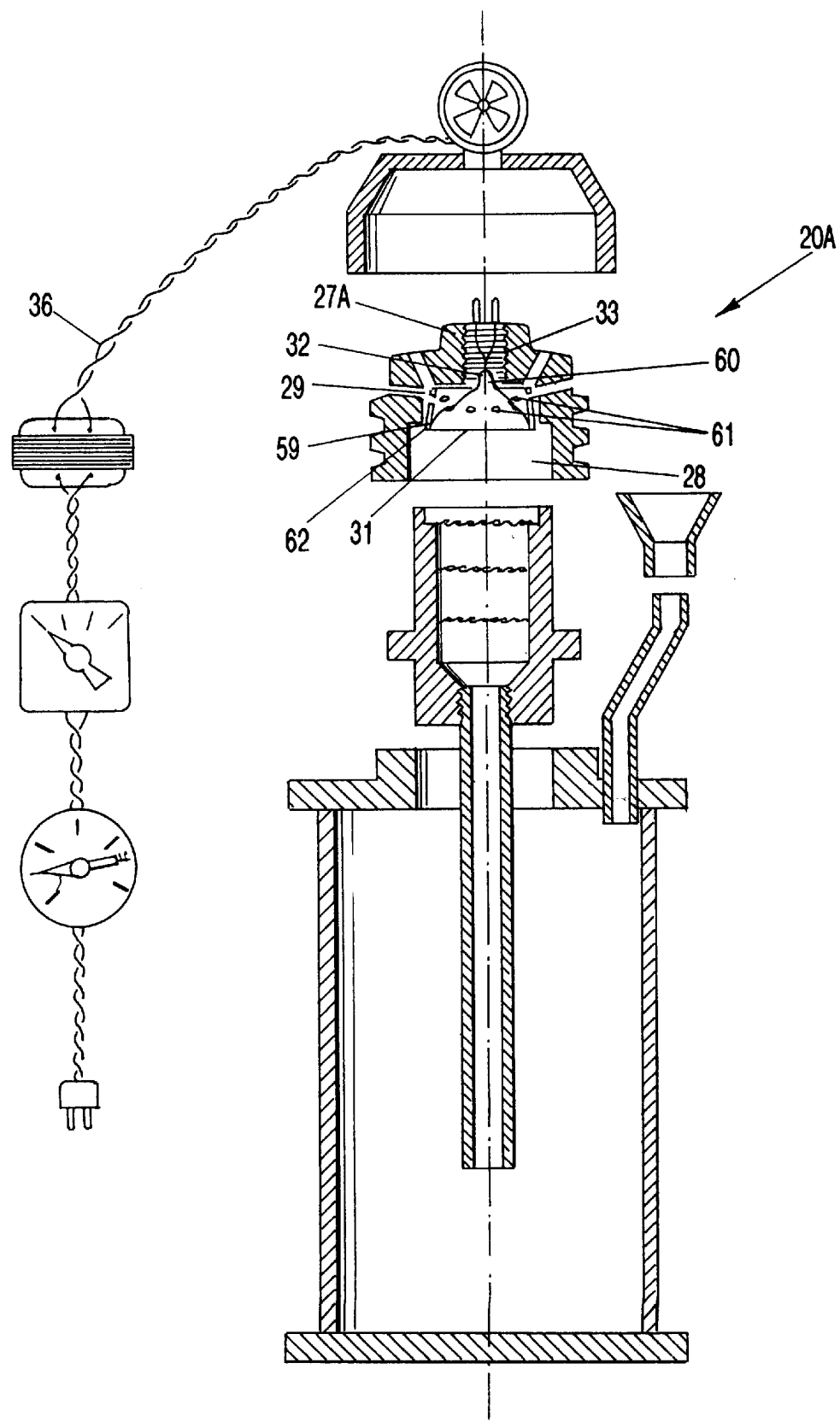
FIG. 2 is a second exemplary embodiment of an inventive extraction device.

The embodiment illustrated in FIG. 2 differs from that shown in FIG. 1 primarily in the configuration and arrangement of the cap 27. For example, the hot air extraction device 20A of FIG. 2 shows a cap 27A wherein an intermediate holder means 59 is provided in order to effect attachment of the heating element 31 to the cap 27A. In particular, this holder means 59 is provided with a threaded part 60, the external threads of which cooperate with internal threads provided in the bore 33 in the upper part of the cap 27A, while the threaded portion 32 of the heating element 31 is screwed into internal threads of the threaded part 60 of the holder means 59. In order to allow air that is entering through the holes 30 of the cap 27A to reach the recessed chamber portion 29 of the cap 27A, and hence to reach the heating element 31, the holder means 59 is also provided with holes 61. In addition, the holder means 59 is spaced from the inner peripheral surface of the chamber portion 29 to form a gap 62 by means of which some of the air entering through the holes 30 passes around the heating element 31, although still being somewhat heated thereby, to pass directly into the chamber 28 of the cap 27A. In other respects, the hot air extraction device 20A of FIG. 2 operates in the same manner as does the hot air extraction device 20 of FIG. 1.

The materials of the various components of the inventive hot air extraction device can vary, depending, for example, upon the application for which the device is to be used, and the conditions to which the device is to be exposed, especially the temperature to which the incoming air or gas is to be heated. Thus, the cap can be made of aluminum, although other materials, such as polymeric material, would also be suitable. The container or bowl 21 can be made of stainless steel, ceramic material, blown glass or polymeric material.

As indicated previously, various cooling means can be provided for the barrel or tank 42. For example, especially for industrial extraction purposes, coolant-containing tubes or a jacket can be provided for the tank 42 in order to allow coolant to circulate around or through the tank.

Although the inventive hot air extraction device has been described in conjunction with drawing or pushing air through the device, it is to be understood that other gaseous substances, especially inert gas, could also be used, again especially for industrial purposes.

Again for industrial purposes, the tank 42 can serve as a collection tank for the volatized material that leaves the container 21 through the discharge opening 44 thereof. In this connection, although the drawings illustrate the discharge opening 44 at the bottom of the container 21, it is to be understood that the discharge opening could be at any other convenient location that leads to a collection tank or the like.

The present invention is, of course, in no way restricted to the specific disclosure of the specification and drawings, but also encompasses any modifications within the scope of the appended claims.

What I claim is:

1. A hot gas extraction device for volatizing at least one substituent of a material, said device comprising:
   a container for holding material and having an open end as well as a discharge opening, said container further having a first chamber that communicates with both said open end and said discharge opening of said container, which discharge opening is disposed remote from said open end;
   a cap having holes leading from an exterior thereof to a second chamber provided within said cap, said cap being disposed on said container such that said second chamber of said cap communicates with said open end, and hence said first chamber, of said container;
   a non-flame electrical heating means disposed in said second chamber of said cap for heating gas; and
   means to cause gas to pass through said holes of said cap, into said second chamber of said cap, downwardly through said first chamber of said container and through said held material placed therein to effect volatization of at least one substituent thereof, and out of said discharge opening thereof.

2. A device according to claim 1, wherein said second chamber of said cap has a first portion that communicates with said open end of said container, and has a second portion of reduced diameter that communicates with said holes of said cap and in which said heating means is at least substantially disposed.

3. A device according to claim 2, wherein said heating means is provided with apertures to allow gas to pass from said second chamber portion through said heating means to said first chamber portion of said cap.

4. A device according to claim 3, wherein an end of said first chamber of said container remote from said open end thereof and adjoining said discharge opening has a tapered-down configuration.

5. A device according to claim 4, which includes a barrel or tank for receiving said container, wherein said discharge opening of said container communicates with an interior of said barrel or tank to convey hot gas thereto, and wherein said barrel or tank is provided with discharge means.

6. A device according to claim 5, wherein said means to cause gas to pass through includes a discharge tube which is connected to said discharge means of said barrel or tank and through which gas can be drawn.

7. A device according to claim 5, which includes cooling means for said barrel or tank.

8. A device according to claim 4, wherein said means to cause gas to pass through includes a fan means disposed on said cap to push gas through at least some of said holes thereof and into said second chamber.

9. A device according to claim 4, which includes at least one screen disposed in said container.

10. A device according to claim 9, which includes one screen to support material, and at least one further screen thereabove.

11. A device according to claim 3, wherein a holder means is disposed in said second chamber portion of said cap and is connected to the latter, wherein said holder means is provided with holes to allow at least a portion of gas entering said holes of said cap to pass to said second chamber portion, and wherein said heating means is supported by said holder means.

12. A device according to claim 11, wherein an annular gap is provided between said holder means and a surface of said second chamber portion of said cap.

13. A device according to claim 3, which includes means to vary the temperature of said heating means.

14. A device according to claim 3, wherein said holes of said cap and said apertures of said heating means are offset relative to one another.

15. A device according to claim 3, wherein said gas is air or inert gas.

16. A device according to claim 1, wherein said means to cause gas to pass through includes means communicating with said discharge opening of said container to draw gas through said device.

17. A device according to claim 1, wherein said heating means is disposed between said holes of said cap and said open end of said container.

* * * * *